(12) United States Patent
Garde et al.

(10) Patent No.: US 6,377,848 B1
(45) Date of Patent: Apr. 23, 2002

(54) DEVICES ACTIVATING AN IONTOPHORETIC DELIVERY DEVICE

(75) Inventors: Kenneth E. Garde, New Windsor, NY (US); Ronald J. Flower, Atlanta, GA (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

(21) Appl. No.: 09/382,900

(22) Filed: Aug. 25, 1999

(51) Int. Cl.[7] ................................................. A61N 1/30
(52) U.S. Cl. ......................................................... 604/20
(58) Field of Search ................................. 607/152, 153; 604/20, 501

(56) References Cited

U.S. PATENT DOCUMENTS

| | | | |
|---|---|---|---|
| 4,808,152 A | | 2/1989 | Sibalis ........................ 604/20 |
| 5,224,928 A | * | 7/1993 | Sibalis |
| 5,314,502 A | | 5/1994 | McNichols et al. ........... 604/20 |
| 5,380,271 A | | 1/1995 | Gyory |
| 5,562,607 A | * | 10/1996 | Gyory |
| 5,645,526 A | * | 7/1997 | Flower |
| 5,693,024 A | * | 12/1997 | Flower |
| 5,830,175 A | * | 11/1998 | Flower |
| 5,857,994 A | * | 1/1999 | Flower |
| 5,978,701 A | * | 11/1999 | Johnson et al. |
| 6,018,680 A | * | 1/2000 | Flower |

* cited by examiner

*Primary Examiner*—Mark Bockelman
(74) *Attorney, Agent, or Firm*—Kirkpatrick & Lockhart LLP

(57) ABSTRACT

An iontophoretic drug delivery device includes a controller normally being in an off or low power consumption state, and a patch including electrodes, a reservoir for holding an ionizable drug for transdermal delivery to a patient and a return reservoir. The patch is removable and electrically connectable to the controller, and delivers the drug to patient when the patch is on the patient's skin and when the controller is switched from the off or low power consumption state to an operational state. This occurs when the patch is connected to the controller and a connector connects a power source to the controller or an activation means signals the controller to switch to the operational state. This feature preserves the battery of the controller.

8 Claims, 10 Drawing Sheets

DEVICES ACTIVATING AN IONTOPHORETIC DELIVERY DEVICE

BACKGROUND

1. Field

The invention relates to devices for activating an electronic controller of an iontophoretic delivery device.

2. Description of Related Art

Iontophoresis is the migration of ions when an electrical current is passed through a solution containing ionized species, usually the ionic form of a drug or other therapeutic agent. One particularly advantageous application of iontophoresis is the non-invasive transdermal delivery of ionized drugs into a patient. This is done by applying low levels of current to a patch placed on the patient's skin, which forces the ionized drugs contained in the patch through the patient's skin.

Passive transdermal patches, such as those used to deliver nitroglycerin for angina pectoris, estradiol for hormone replacement, and nicotine to stop smoking, can only use a limited number of drugs because they work by diffusion. Iontophoresis advantageously expands the range of drugs available for transdermal delivery, including, for example, parenteral drugs (e.g., peptides). Further, because the amount of drug delivered is proportional to the amount of current applied, the drug delivery rate can be precisely controlled by controlling the current, unlike the passive transdermal patches. This allows for more rapid delivery (onset) and drug reduction (offset) in the patient.

When compared to drug delivery by needle injection, iontophoresis has less physical and emotional trauma, pain and possibility of infection. Transdermal drug delivery by iontophoresis also avoids the risks and inconvenience of intravenous delivery. In addition, when compared to oral ingestion of drugs, drug delivery by iontophoresis bypasses the GI tract, thus reducing side-effects such as drug loss, indigestion and stomach distress and eliminating the need for swallowing the drug. Iontophoresis also avoids drug loss due to hepatic first pass metabolism by the liver that occurs when drugs are ingested.

Further, transdermal drug delivery by iontophoresis permits continuous delivery of drugs with a short half life and easy termination of drug delivery. Because iontophoresis is more convenient, there is a greater likelihood of patient compliance in taking the drug. Thus, for all of the above reasons, iontophoresis offers an alternative and effective method of drug delivery, and is a especially useful method for children, the bedridden and the elderly.

An iontophoretic drug delivery device includes a current source, such as a battery and current controller, and a patch. The patch includes an active reservoir and a return reservoir. The active reservoir contains the ionized drug, usually in a conductive gel. The return reservoir contains a saline gel and collects ions emanating from the patient's skin when the drug is being delivered into the patient's skin.

The patch also has two electrodes, each arranged inside the active and return reservoirs to be in respective contact with the drug and saline. The anode, or positive, electrode and the cathode, or negative, electrode are respectively electrically connected to the anode and cathode of the current source by electrical conductors. Either the anode electrode or the cathode electrode is placed within the drug reservoir, depending on the charge of the ionized drug. This electrode is designated as the active electrode. The other electrode is placed within the return reservoir, and is designated as the return electrode.

The active electrode has the same charge as the ionized drug to be delivered and the return electrode has a charge opposite the drug to be delivered. For example, if the drug to be delivered to the patient has a positive ionic charge, then the anode will be the active electrode and the cathode will be the return electrode. Alternatively, if the drug to be delivered has a negative ionic charge, then the active electrode will be the cathode and the return electrode will be the anode.

When current from the current source is supplied to the active electrode, the drug ions migrate from the drug gel in the reservoir toward and through the skin of a patient. At the same time, ions flow from the patient's skin into the saline solution of the return reservoir. Charge is transferred into the return electrode and back to the current source, completing the iontophoretic circuit.

For example, in an iontophoresis device employing a negatively-charged drug ion $D^-$, the drug reservoir houses the cathode and ionized drug $D^-$, and the return reservoir houses the saline solution and the anode. Upon application of current to the electrodes, negatively-charged drug ions are repelled from the cathode, because the drug ions and the cathode have the same negative polarity, and flow through the patient's skin. At the same time, positively-charged ions flow back into the drug reservoir, being attracted to the cathode, and negatively-charged ions flow from the skin into the return reservoir, since they are attracted to the anode.

An electronic current controller between the battery and the electrodes regulates the current from the battery so that the patch receives the correct amount of current to deliver the proper dosage. This controller may control the current output to the patch so that drug delivery is accomplished at a constant or varying rate, or over a short, long or periodic time interval. These controllers generally require relatively complex electrical circuits, sometimes including microprocessors, to meet the above requirements.

Mechanical switches have been used in controllers to disconnect the battery from the controller circuitry to prevent battery drain during device storage. These controllers need to be switched on at the time they are placed on the body in order to begin operating. This, however, may lead to delayed drug delivery because the physician, nurse or patient may not remember to turn on the switch, or to erroneous drug delivery if the switch is inadvertently turned off before the completion of the drug delivery cycle. In addition, in the case of a defective switch or a switch having poor electrical contact, there may be uncertainty as to whether or not the device is actually delivering the therapeutic agent, or whether or not the device can complete without interruption an entire drug delivery cycle.

Electrically-activated switches have also been used to turn on iontophoretic drug delivery devices. See, for example, the switch 80 shown in FIG. 2 of U.S. Pat. No. 4,808,152 (Sibalis), which activates the iontophoretic device when electrical contact is made between the skin and the electrode. See also U.S. Pat. No. 5,314,502 (McNichols et al.), which shows an iontophoretic device including a two-electrode patch, electronic activation circuitry and power generating circuitry. The device remains completely turned off until the patch is applied to the skin. At that time, the circuit between the patch electrodes closes, closing the electronic activation circuitry and causing the power generating circuitry to be activated, thereby activating the iontophoretic device. Because the touching of the skin acts as the switch, a mechanical switch is not required. This type of switch is also said to prevent current drain from the battery during device storage.

However, a problem may still exist because the device may be activated when in contact with a conductive surface other than a patient's skin. In this case, the circuit between the electrodes will close and the device will be activated, resulting in the unnecessary waste of the therapeutic drug and generating uncertainty in the ability of the device to deliver an entire drug dosage. Another problem of iontophoretic devices using mechanical switches or touch-sensitive switches is that these devices are turned on manually. Because of this, multiple iontophoretic devices using mechanical switches or touch-sensitive switches cannot easily be turned on simultaneously, nor can an iontophoretic device be turned on remotely.

In addition, these switches do not take into consideration other factors which are important in iontophoretic drug delivery systems. For example, it is well known that the electrical impedance of epidermal skin tissue ("skin impedance") varies greatly, depending on factors such as where the patch is applied onto the body, the presence of calluses or dermal abrasions at that location, ambient air conditions such as temperature and humidity, the amount of skin hydration caused by perspiration, and the age of the individual. Skin impedance also varies as the current flows during iontophoretic drug delivery. For example, an extremely dry skin-patch interface is undesirable and problematic because it results in a unusually high impedance, requiring too high of a voltage to maintain the proper current level. Alternatively, when a voltage within the device's normal voltage range is applied to a high impedance load, a current well below the proper current level will result. Any of the above operating conditions may cause skin irritation or may reduce drug transport.

Other problems that may arise in turning on iontophoretic devices by the above-described conventional methods involve the delivery of drugs or medicaments containing peptides. These problems are caused by the ionic charge of the peptide at the pH level of the skin, or by ionic, hydrophobic or biological interactions between the peptide and skin proteases. Skin proteases are enzymes that break the peptides into their constituent components and are carried, for example, by a person's perspiration. Both factors may reduce the peptide's mobility and thus impair its delivery.

SUMMARY OF THE INVENTION

Accordingly, there is a need for improved methods of activating iontophoretic devices so that the user of the iontophoretic device has greater control of the device, as well as increased flexibility and reliability.

It is an object of the present invention to provide methods for turning on an iontophoretic drug delivery device that overcome the above-described problems. Activation of the iontophoretic drug delivery system may be based on one or more of the above-described factors that cause variations in skin impedance. Activation of the iontophoretic device may also based on the skin's pH or the amount of skin perspiration, or both, to overcome problems when delivering peptides. Activation may also be based on other factors external to the controller that may influence the operation of the controller, such as gravity or certain environmental conditions.

It is another object of the present invention to provide an iontophoretic drug delivery device that prevents unintended power-drain when conventional mechanical switches or touch-sensitive switches are used.

In is still another object of the present invention to provide an iontophoretic drug delivery device that can be turned on remotely or to allow multiple iontophoretic drug delivery devices to be turned on simultaneously.

In one aspect of the present invention, an iontophoretic drug delivery device is provided which includes (1) a controller normally in an off or low-power consumption state, and (2) a patch including (a) a pair of electrodes, (b) an active reservoir for holding an ionizable drug for transdermal delivery to a patient and (c) a return reservoir. The patch is removable and electrically connectable to the controller, and delivers the drug to the patient when the patch is on the patient's skin and when the controller is switched from the off or low-power consumption state to an operational state. This switching may be caused by electrically connecting the patch to the controller and activating a connector therebetween. This switching may also be caused by electrically activating an activation signal circuit connected to the controller.

BRIEF DESCRIPTION OF THE DRAWINGS

These and other objects, features and advantages of the present invention can best be understood by reference to the detailed description of the preferred embodiments set forth below taken with the drawings, in which.

DETAILED DESCRIPTION OF THE PREFERRED EMBODIMENTS

Figure 1:
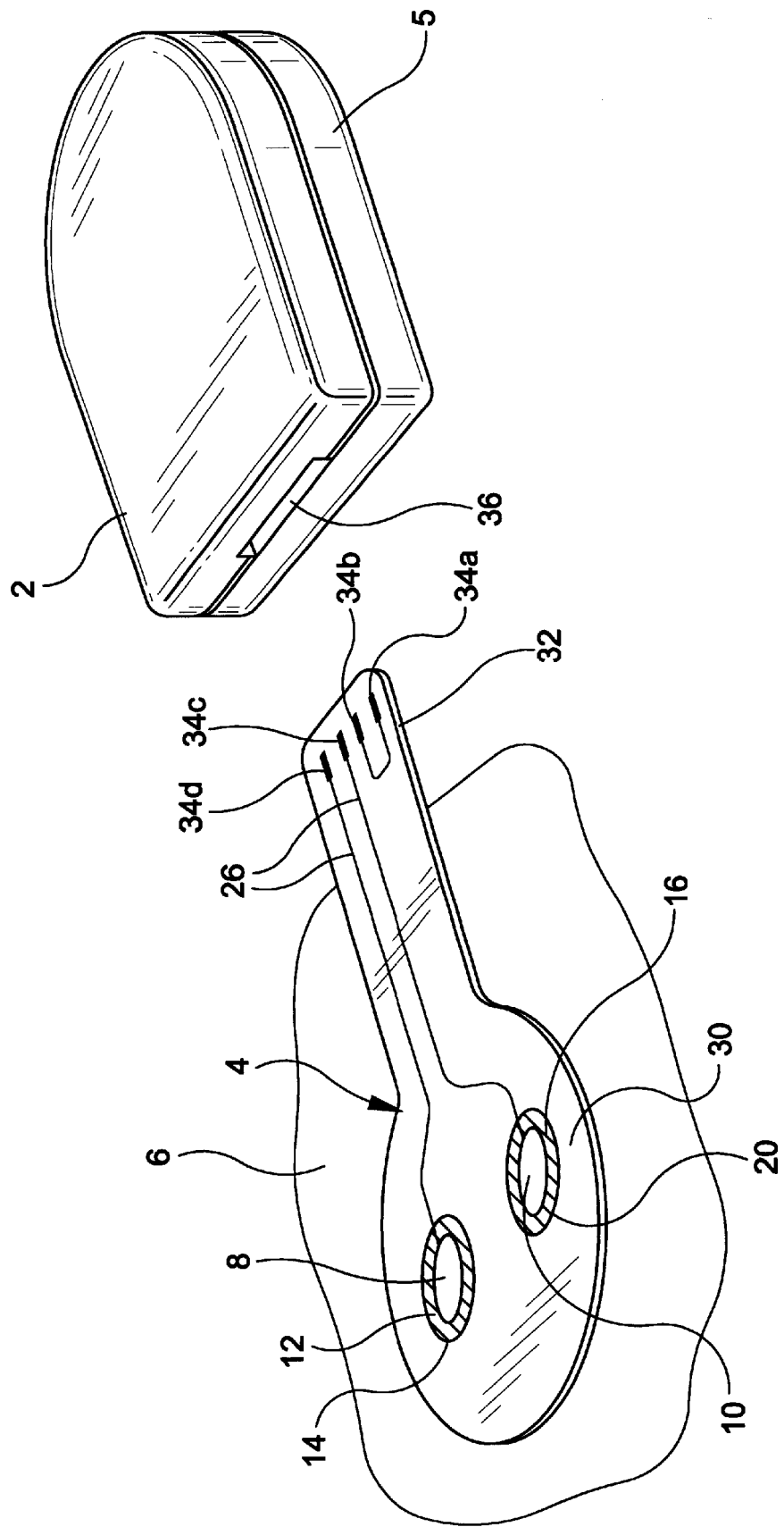
FIG. 1 is a perspective view of an iontophoretic drug delivery device in accordance with the present invention.

An iontophoretic drug delivery device in accordance with the present invention, as shown in FIG. 1, includes a separate, reusable controller 2, which can be removably and electrically connected to a patch 4 containing the drug, therapeutic agent or medicament. The patch 4 is attached to the skin 6 of the patient. The patch includes active electrode 8 and a return electrode 10. An ionic drug gel 12, in solution or suspension, and the active electrode 8 are positioned in an active reservoir 14. An electrolytic gel 16, such as saline, and the return electrode 10 are positioned within a return reservoir 20. Other formulations or carriers of the ionic drug and return electrolyte may also be used, as are well-known in the art.

Figure 2:
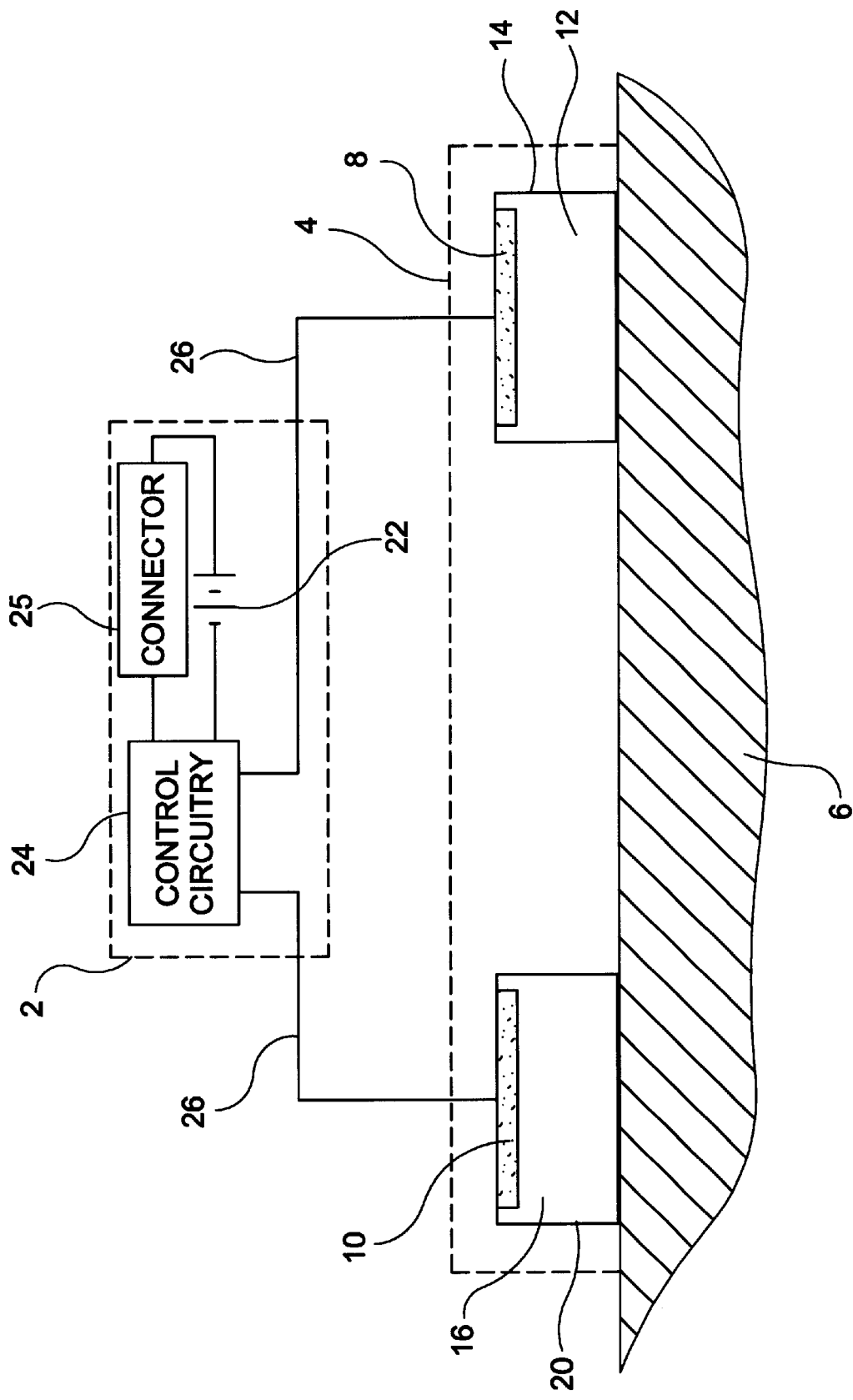
FIG. 2 shows a block diagram of an iontophoretic circuit in accordance with a first embodiment of the present invention.

As shown in the FIG. 2, the controller 2 has a power source 22, such as a battery, and control circuitry 24. The controller 2 is electrically coupled to the patch 4 using electronic interconnectors 26, such as a printed flexible circuit, metal foils, wires, tabs or electrically conductive adhesives. When connector 25 is in a connected state, the power source 22, the electrodes 8 and 10, the control circuitry 24 and the patient's skin 6 form a circuit, thereby generating an electric field across the skin on which the iontophoretic device is applied. The electric field causes the ionic drug 12 in the active reservoir 14 to be delivered into the body of the patient by iontophoresis.

Patch 4 is generally a planar flexible member formed of, for example, a biocompatible material such as woven or non-woven textiles or polymers, or any other construction well-known in the art. The patch 4 is attached to the patient's skin 6 using adhesives or a strap or both. The patch 4 includes an enlarged patch body 30, which includes the active reservoir 14 and the return reservoir 20, and an extending tab 32, which connects to the controller 2.

The lower surface of the reservoirs 14 and 20 are placed in contact with the skin 6, allowing the electrodes 8 and 10 to be very close to the skin 6 when the patch 4 is attached on the patient. Generally, a thin layer of the gel in the reservoirs will be between the skin and the electrodes. The electrodes are positioned so that an ionic circuit path is established between the electrodes 8 and 10 through the patient's skin 6. A current source is connected to the electrodes 8 and 10 so that the active electrode 8 has the same charge polarity as the ionic drug 12. When current passes through the electrodes 8 and 10, the drug ions contained in the active reservoir 14 is delivered through the skin 6 and into the patient.

Figure 4:
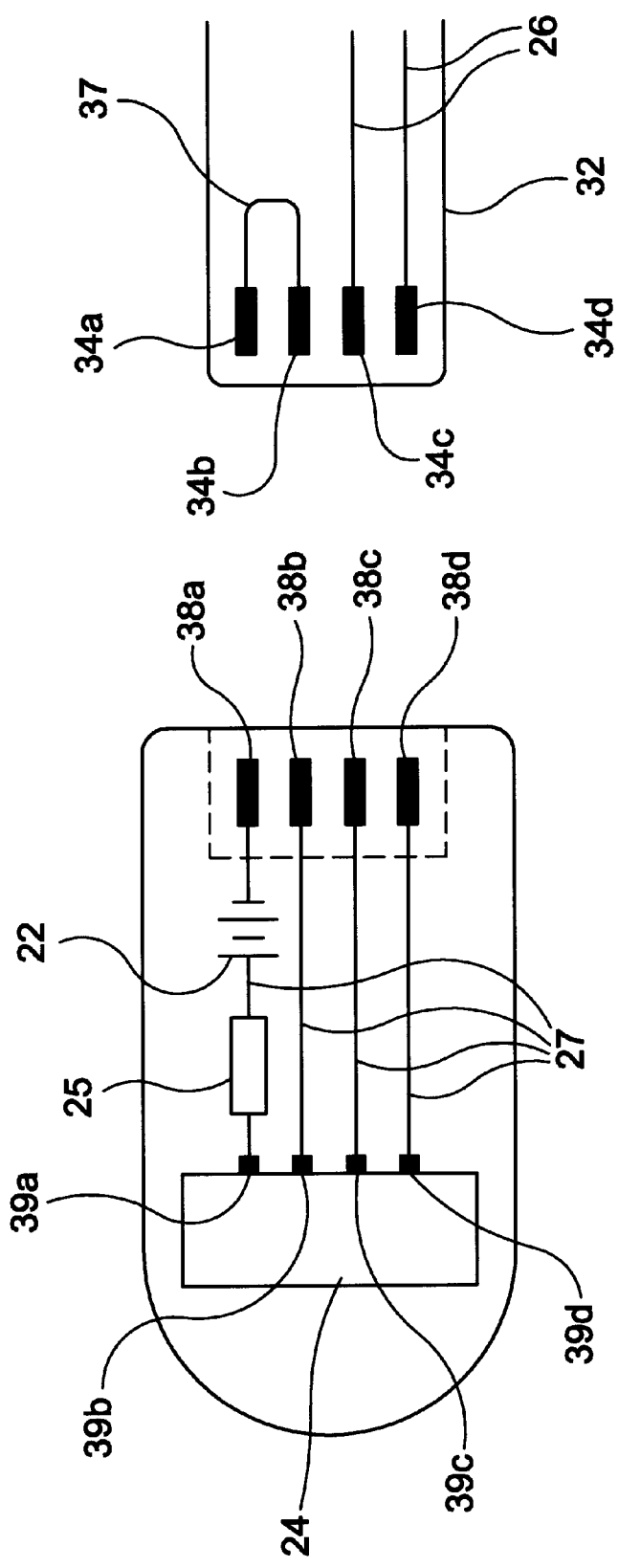
FIG. 4 shows a patch/controller switch in accordance with the present invention.

The patch also includes an extending tab 32, as shown in FIG. 4, substantially including the electrical connectors 26. The electrical connectors 26 may be one or more conductive paths extending from the electrodes 8 and 10 to exposed conductive pads 34a–34d positioned on the marginal edge of the extended patch tab 32. The pads 34a–34d are positioned for electrical connection with the controller 2 when the extending patch tab 32 is inserted into the controller 2, thereby providing the electrical connection between the patch electrodes and the controller 2.

The controller 2 has a housing 5 that is generally rectangular or oval in shape, with rounded edges, and has an opening in the front end to accommodate the inserted patch tab 32. The housing 5 also has connection arrays 38 and 39 of electric terminals 38a–38d and 39a–39d to which the control circuitry 24 and power source 22 are electrically connected through electrical connectors 27, and are preferably mounted with the electric circuits on a printed circuit board. The plural, spaced apart electrical terminals 38a–38d electrically connect to the respective patch tab pads 34a–34d. While, the plural, spaced apart electrical terminals 39a–39d electrically connect the power source 22 and electrical connectors 27 to the control circuitry 24. Electrical terminals 39a and 39b are power terminals, and electrical terminals 39c and 39d are output current terminals. However, any suitable electrical interconnection device may be employed instead. Further, it may be appreciated that the patch insertion and release mechanisms may take any known form, so long as the patch tab 32 is capable of being mechanically and electrically connected to and disconnected from the controller 2.

Figure 3:
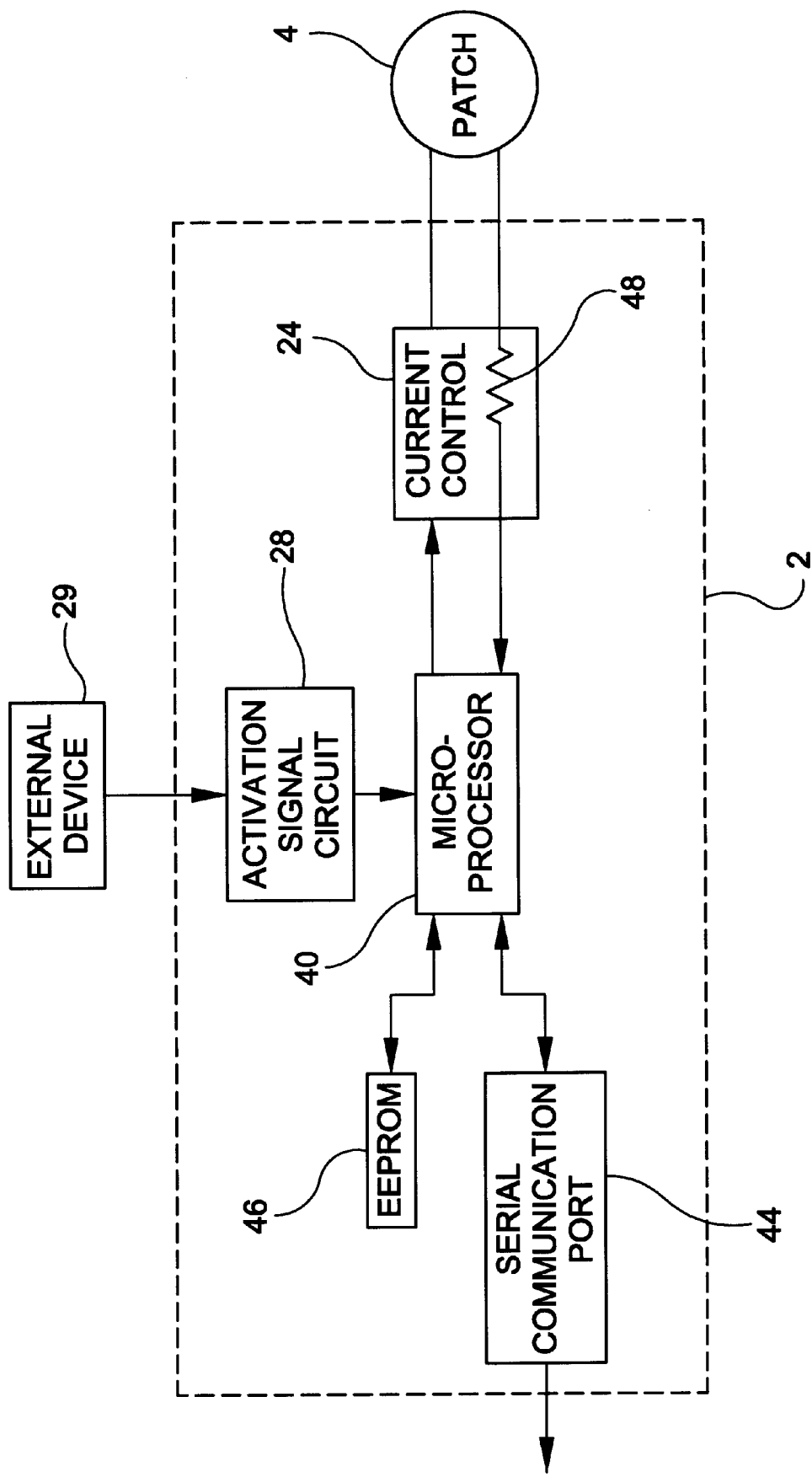
FIG. 3 shows a block diagram of a controller in accordance with a second embodiment of the present invention.

The controller 2 may include, but is not limited to, a power source 22, a microprocessor 40, EEPROM 46, a serial communication port 44 and control circuitry 24, as shown in FIG. 3. The microprocessor 40 generates signals to the control circuitry 24 to ensure that the required current is delivered by the control circuitry 24 to the connected patch 4 through conductors 27 and 26 to electrodes 8 and 10 so that the correct amount of drug is delivered to the patient. The control circuitry 24 generates the required output current irrespective of the varying load impedance.

Further, voltage from a sensor, such as a current sense resistor 48, is monitored by the control circuitry 24 to ensure that the amount of delivered current is correct. The current passing through the current sense resistor 48 is the same as the current being delivered through the iontophoretic patch 4 and skin 6. If less or more than the required current is being delivered to the patient, as indicated by the current sense resistor, the control circuitry 24 adjusts the current to the required level.

As shown in FIG. 4, the control circuitry 24 is kept completely turned off so that the power source 22 is not drained accidentally or unnecessarily. The control circuitry 24 is electrically and mechanically connected to the patch 4 by the insertion of the patch tab 32 into the controller 2. The cathode of the power source 22 is connected to one end of the connector 25 and the anode of the power source 22 is connected to the controller electrical terminal 38a (of course, the cathode and anode may be reversed, depending upon the desired polarity). The other end of the connector 25 is connected to a first battery terminal of the control circuitry 24. A second input terminal of the control circuitry 24 is connected to electrical patch terminal 38b. Because the electrical patch terminals 38a and 38b are unconnected to each other, the circuit is open, and the control circuitry 24 is off.

When the patch is inserted into the controller in slot 36, an electrical jumper 37 on the extended patch tab 32, connected between pads 34a and 34b, electrically connects terminals 38a and 38b. However, the control circuitry 24, including the microprocessor 40, does not turn on until the connector 25 is activated. Activation of the connector 25 completes the circuit and thus connects the power source 22 to the control circuitry 24. Alternatively, the connector 25 can be activated before the patch 4 is inserted into the controller 2. Once the patch is inserted, the controller will be fully turned on. Further, the terminals 38a and 38b may be eliminated and replaced by a short. This makes patch insertion irrelevant to turning on the device, and the controller is turned when only the connector 25 is activated.

Figure 8A:
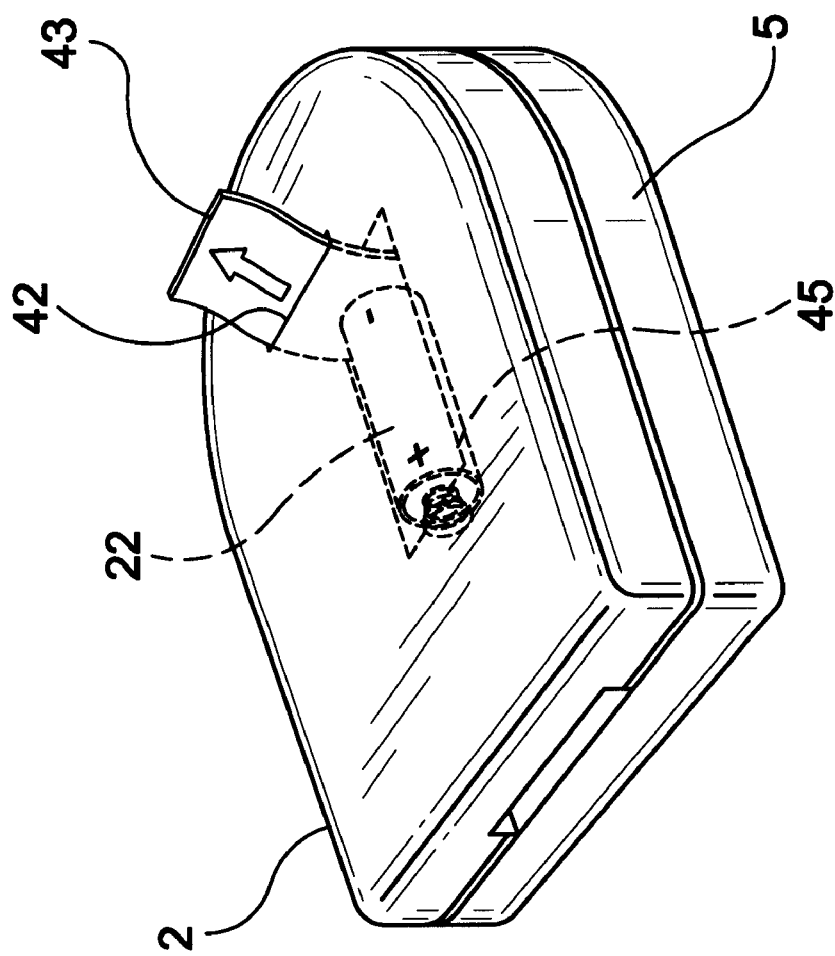
FIGS. 8A, 8B and 8C show various pull tab arrangements in accordance with the present invention.

In one embodiment of the present invention, the connector 25 is a pull tab 43 made of a electrical insulator, as shown in FIG. 8A. The pull tab 43 is physically inserted as a non-conducting barrier between the cathode of the power source 22 and the first battery terminal of control circuitry 24. A portion of the pull tab 43 extends outside the controller through a slot 42 in the housing 5. A spring force, such as that provided by a battery holder 45, urges the power source 22 against the pull tab 43 and toward the first battery terminal to prevent the pull tab 43 from too easily being removed from the housing. When the user removes the pull tab 43 from the controller by pulling on the extended portion, the spring force urges the power source 22 against the first battery terminal of the control circuitry 24 causing electrical contact, and thus the connector 25 is activated.

The pull tab 43 ensures that the power source 22 is not being drained prior to the user removing the pull tab 43. This is advantageous when the manufacturer of the iontophoretic drug delivery device ships the device with batteries in place, or with the patch 4 connected to the controller 2, or both. The pull tab 32 may be constructed so that once it has been removed, it can be either reinserted or not reinserted by the user. For example, the pull tab 43 may be made from a flexible insulation material which cannot be reinserted because it cannot overcome the spring force holding the power source 22 against the first battery terminal. Alternatively, the pull tab may be made of a rigid insulation material that can be reinserted between the power source 22 and the first battery terminal.

Figure 8B:
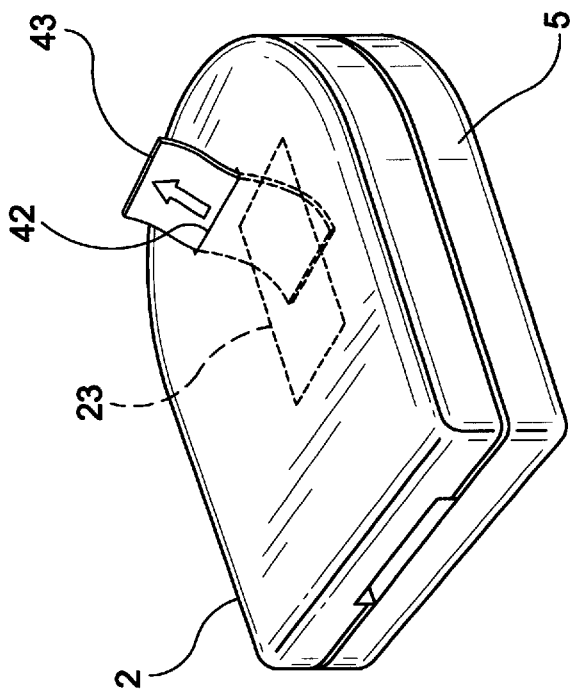

In another embodiment of the present invention, the connector 25 is the pull tab 43 used to activate a zinc/air battery 23, as shown in FIG. 8B. The zinc/air battery 23 uses oxygen directly from the surrounding air to produce electrochemical energy. This battery is hermetically sealed to prevent contact with the air and thus accidental power drain. In this embodiment, the pull tab 43 is hermetically sealed with the zinc/air battery 23, with a portion of the pull tab 43 extending from the slot 42 in the controller housing 5. The user activates the connector 25 by pulling the pull tab 43 out of the housing; thus breaking the hermetic seal and allowing air into the zinc/air battery 23.

Figure 8C:
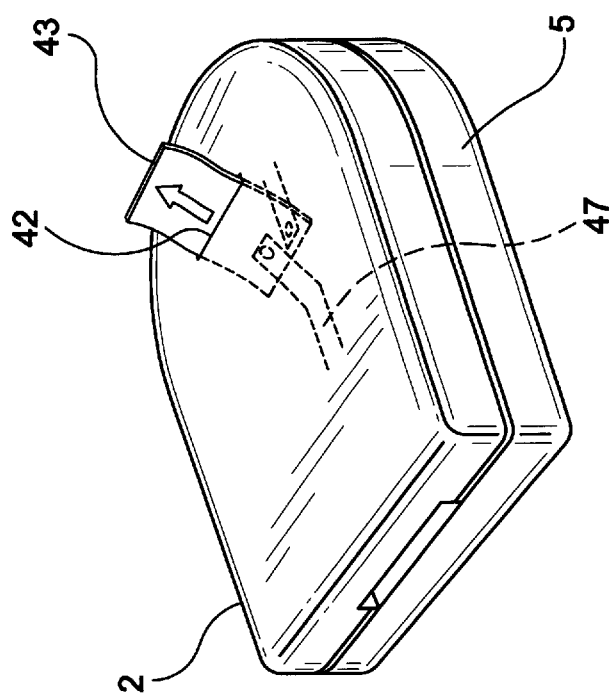

In yet another embodiment of the present invention, the connector 25 is a pull tab 43 and a mechanical switch 47 arranged within the controller 2, as shown in FIG. 8C. The mechanical switch 47 is arranged in series between the power source 22 and the first battery terminal of the controller circuitry. In this embodiment, the pull-tab 43 is a non-conductive electrical insulator inserted between the make/break contact of the mechanical switch 47. A portion of the pull tab 43 extends outside the controller housing 5 through the slot 42. When a user pulls the extending portion and removes the pull tab 43, the mechanical switch 47 becomes fully operational. If the switch 47 is normally open, the user may then close the mechanical switch 47 to activate the controller 2. Alternatively, if the switch is normally closed, the controller 2 is activated upon pulling out the pull tab 43.

Once again, the pull tab 43 ensures that the power source 22 is not being drained, for example, when a connected patch 4 is accidentally placed on a conductive surface or when the mechanical switch 47 is unintentionally switched to the "on" position, preventing the unnecessary waste of the drug and ensuring that a full delivery cycle can be completed.

In yet another embodiment, the connector 25 includes a pressure switch or pressure transducer circuit. A pressure switch is actuated by a change in the pressure of a gas or liquid. Using a pressure switch to activate the controller 2 is particularly useful in situations where the user of the iontophoretic drug delivery device is at high altitudes, below sea level or underwater. For example, the user can be a pilot or a passenger on an airplane, or a scuba diver. In these situations, the pressure switch is arranged between the power source 22 and the first battery terminal of the control circuitry 24, and is activated due to a change in ambient pressure. This may be beneficial when using the iontophoretic device to delivery therapeutic drugs to counteract air sickness or nitrogen narcosis.

Figure 5:
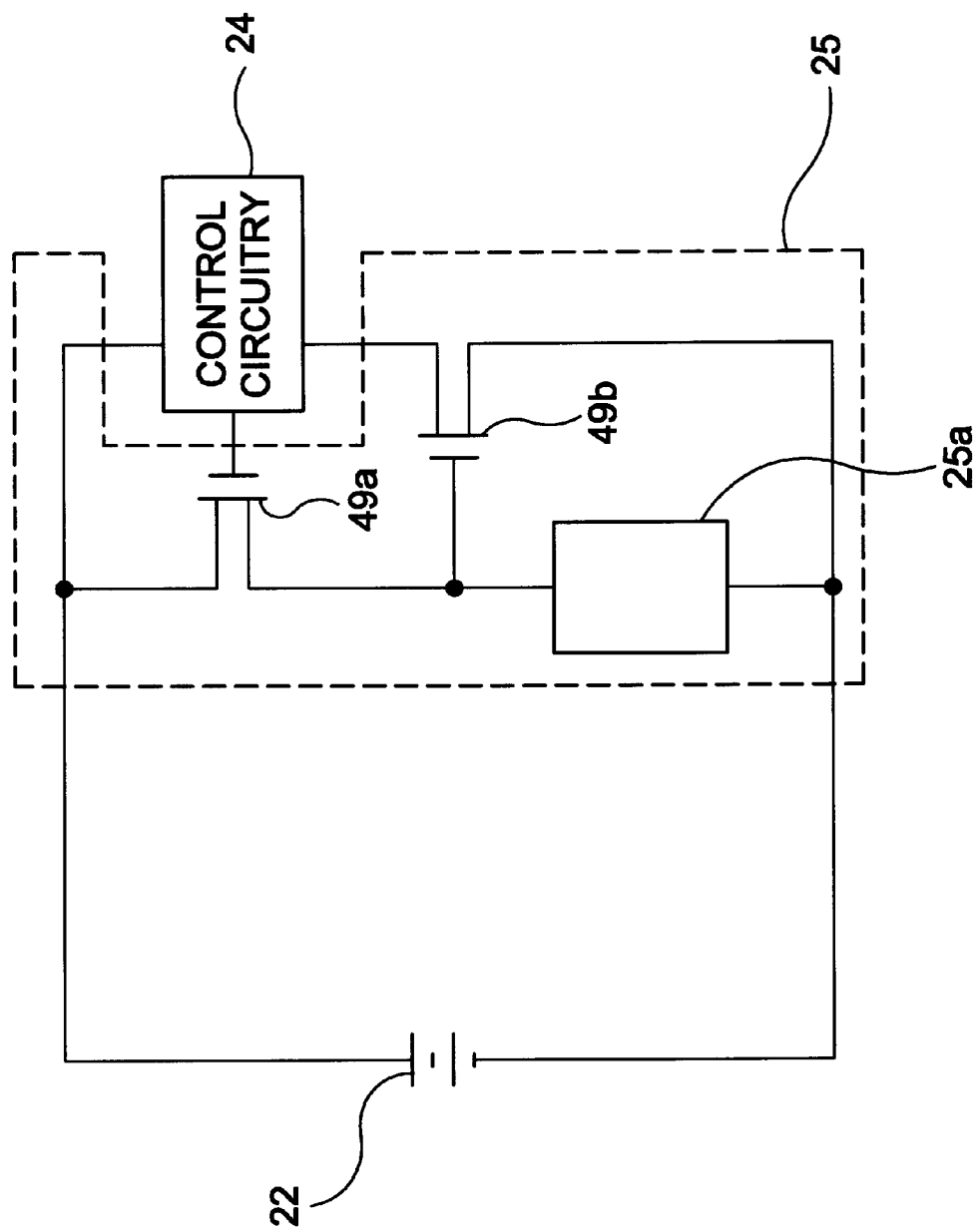
FIG. 5 shows a latching circuit in accordance with the present invention.

Alternatively, a pressure transducer circuit may be used. A pressure transducer is an instrument, which converts a static or dynamic pressure input to the transducer into a proportional electrical output. As shown in FIG. 5, when the pressure transducer 25a senses a change in pressure, it produces an electrical current, which biases the gate of a field effect transistor (FET) 49b. FET 49b then turns on and completes the circuit (by allowing current to flow through the source and drain of the FET) and connects the power source 22 to the control circuitry 24.

A latching circuit may be used to ensure that electrical power remains turned on (i.e., that the power source 22 remains connected to the control circuitry 24) even after the pressure change is removed, as follows. After activation, control circuitry 24 provides a signal to the gate of FET 49a to bias that gate and activate the FET 49a. The current passing through FET 49a biases the gate of FET 49b, even after any biasing signal from pressure transducer 25a has gone away, which ensures that FET 49b remains turned on. The latching circuit can be deactivated by momentarily disconnecting the power source 22 from the controller 2. This can be done by the controller 2, via a relay or other means (not shown) after the drug delivery cycle is complete. If the latching FET 49a is not provided, the power source 22 will remain connected to the control circuitry 24 only as long as the signal from the pressure transducer 25a is biasing the FET 49b (i.e., the activating pressure is maintained). It will be appreciated by one of ordinary skill in the art that other types of latching circuits can be used, for example, the FETs can be replaced with bipolar transistors and/or relays can be used instead of FETs.

A pressure transducer can also be used to sense changes in the blood pressure of a person. In this case, the iontophoretic controller activates based on predetermined changes in blood pressure to deliver, for example, high- or low-blood pressure medication to the person. The pressure switch/transducer may also be used with a suction cup device or vacuum pump device to form a vacuum between the user's skin and the pressure switch or transducer. In this case, the iontophoretic drug delivery device activates when the vacuum is formed.

In yet another embodiment, the connector 25 is a photoelectric device, such as a phototransistor or photodiode. In particular, the phototransistor or photodiode may be substituted for the pressure transducer as element 25a in FIG. 5. A phototransistor is a light-sensitive transistor that delivers an electrical output proportional to the light intensity at its input (i.e., its base or gate). The generated photocurrent is amplified by the current gain of the transistor. In this embodiment, the phototransistor generates an electric current when illuminated by light, which in turn triggers the above-described latch circuit connecting the power source 22 to the control circuitry 24. As will be understood by one skilled in the art, photodiodes, photocells and photodetectors, for example, may also be used to trigger the latch circuit of FIG. 5. The intensity and wavelength of light incident on the photoelectric device required to trigger the latch circuit is controllable. For example, the phototransistor may be designed to respond to daylight, incandescent light, fluorescent light, or a high-intensity light directed toward the photoelectric device. The photoelectric device may also be selected to operate using visible light, infrared light, ultraviolet light or light of other wavelengths, or in any combination thereof. In addition, the photoelectric device may be triggered by the light from a fiber optic cable. For example, a heath-care facility may have one or more fiber optic cables installed in patient rooms. In this example, each iontophoretic drug delivery device may have a fiber optic cable connection to direct light upon the photodetector 25a. A heath-care provider may activate remotely one or more iontophoretic drug delivery devices by sending light, via the fiber optic cables, to the particular devices.

In yet another embodiment, the connector 25 is a magnetic switch that is magnetically activated. A magnetic switch consists of contacts formed by two thin, movable, magnetically actuated metal vanes or reeds, held in normally open position within a sealed glass envelope. Magnetic switches switch to the closed position by the motion of an external magnet moved with respect to the glassed envelope. Thus, in this embodiment, drug delivery can be activated by placing or moving a magnet over the magnetic or magnetic switch. Similarly, a Hall-effect switch may also be used as the connector 25. A Hall-effect switch comprises a Hall generator, trigger circuit, and amplifier. When the Hall-effect switch is actuated, a magnet shunt member is moved across the switch. This increases the magnetic flux through the switch, and causes the analog voltage generated by the Hall element to switch the trigger circuit to the "on" state. When the Hall-effect switch is in the on state, the power source 22 is connected to the control circuitry 24.

Alternatively, the element 25a in FIG. 5 can comprise an inductive coil. When a second inductive coil is placed near the inductive coil 25a, an electrical current is generated, through inductive coupling, which will trigger the latch circuit. The second inductive coil may be, for example, positioned within hospital equipment, such as a diagnostic monitor or some kind of test equipment. Thus, a therapeutic drug can be delivered when a particular medical test is being performed on a patient or a particular monitor is connected to the patient.

In yet another embodiment, the element 25a may be a piezoelectric material, which generates an electrical output when subjected to a mechanical strain (e.g., being hit, bent or twisted). In particular, striking the piezoelectric device 25a in FIG. 5 produces a voltage that causes a current which triggers the latching circuit so that the power source 22 is electrically connected to the control circuitry 24. In another example, a wrist band made of piezoelectric material may be used to produce a current when bent around the wrist of the iontophoretic drug delivery device user.

In yet another embodiment, the connector 25 may be an electromagnetic signal receiver such as low-power AM or FM radio frequency receiver. In this case, the radio receiver receives radio frequency transmissions which are demodulated to determine if the power source 22 should be connected to the control circuitry 24. For example, if a specific signal is received, an output of the radio receiver triggers the latch circuit in FIG. 5. The modulated signal may be any well-known analog or digital signal. Radio receivers/demodulators are also well known in the art and are not described in detail herein. Other types of signal receivers can also be used, such as a global positioning satellite (GPS) receiver. The GPS system is an array of satellites maintained by the U.S. Department of Defense, which transmits navigational and timing information to the earth. The timing information is based on Greenwich Mean Time. The connector 25 may be a low-power GPS receiver which connects the power source 22 to the control circuitry 24, for example, by triggering the latch circuit, at a predetermined time or location based on a received GPS signal. Other timing mechanisms may be used in place of the GPS signal, such as an internal clock circuit, a hardware timing circuit or executable software. Drug delivery may begin at set times or after a predetermined time has elapsed from some predetermined event, such as after connecting the patch 4 to the controller 2, after initial power-up, or after opening the shipping packaging of the device.

The activation techniques of the this embodiment are advantageous because a plurality of iontophoretic drug delivery devices can be activated (1) simultaneously, (2) remotely and/or (3) at a predetermined times. A health care-provider can activate, for example, all the devices in a given geographic region when needed or desired. Thus, one particular device or a particular group of devices can be activated by transmitting a signal specific to those devices. Alternatively, the device or devices can be activated automatically at predetermined times using the GPS receiver or an internal timer.

In yet another embodiment, the connector 25 is a vibration or accelerative force detector. More specifically, an accelerometer, which is a sensor that produces an electrical output proportional to acceleration, may be used. In this embodiment, when an accelerometer is used as the connector 25 in FIG. 5, the latch circuit is triggered by a change in velocity (sudden violent movement) or vibration (shaking) of the controller 2. Accordingly, drug delivery can be initiated by the movement or acceleration of a train, plane, automobile, bicycle, as well as running or shaking the controller 2.

In yet another embodiment, the connector 25 is a mercury switch, which uses gravity as an activation technique. Such a switch can also be used to trigger the latch circuit of FIG. 5. A mercury switch is a switch operated by tilting or vibrating which causes an enclosed pool of mercury to move, making or breaking physical and/or electrical contact. A circuit comprising a mercury switch can trigger the latch circuit, for example, when moved in the horizontal or vertical position or by being moved in a particular manner. Thus, drug delivery can be activated by tilting or moving the controller 2. The controller 2 (when attached, held or worn by a user) may also be activated by having the user stand up, sit down or lay down. Thus, drug delivery can be initiated by a user going to bed at night (i.e., lying down) or getting up in the morning (i.e., standing up).

In yet another embodiment, the connector 25 is a sound detection circuit including an acoustic transducer. The acoustic transducer produces an electrical signal in response to sound that can be used to trigger the latch circuit of FIG. 5. Of course, other types of sound detection circuits may be used, such as, a microphone coupled to a digital signal processor (DSP) with voice recognition software used to detect specific voice patterns (words) or even the voice of a particular person. Other types of sound-sensing circuits can be used to detect specific frequency tones or patterns. These types of sound detection circuits are known in the art and are not described in detail herein.

The connector 25 may also be a temperature detector, a thermal sensor (thermistor or thermocouple), a temperature relay or a solid state temperature sensing device. A circuit using a temperature detector or thermal sensor may be used to trigger the latch circuit of FIG. 5 when the ambient temperature or body temperature of a person reaches a predetermined threshold. These devices are well known in the art and are not described in detail. Likewise, a temperature relay may be used to connect the power source 22 to the control circuitry 24 when the ambient temperature and/or body temperature of a person is at a predetermined temperature. For example, when a person's body temperature reaches 102 degrees Fahrenheit, delivery can be initiated to deliver a drug to suppress fever. Thus, the iontophoretic device delivers the drug directly in response to a temperature indication from a user's body.

The connector 25 may also be a switch activated by the presence or absence of a predetermined gas or gases, e.g., air, nitrogen or carbon dioxide. For example, the connector 25 may activate when the amount of carbon dioxide in the general vicinity reaches a predetermined level. The connector 25 may also be used to automatically activate the iontophoretic drug delivery device when it is removed from its shipping or manufacturing packaging. The device may be hermetically sealed in a pouch filling with only a specific gas (i.e., nitrogen). When the pouch's seal is broken, the device is exposed to air (i.e., oxygen) causing the gas sensor switch to close which will, in turn, activate the device.

Figure 6:
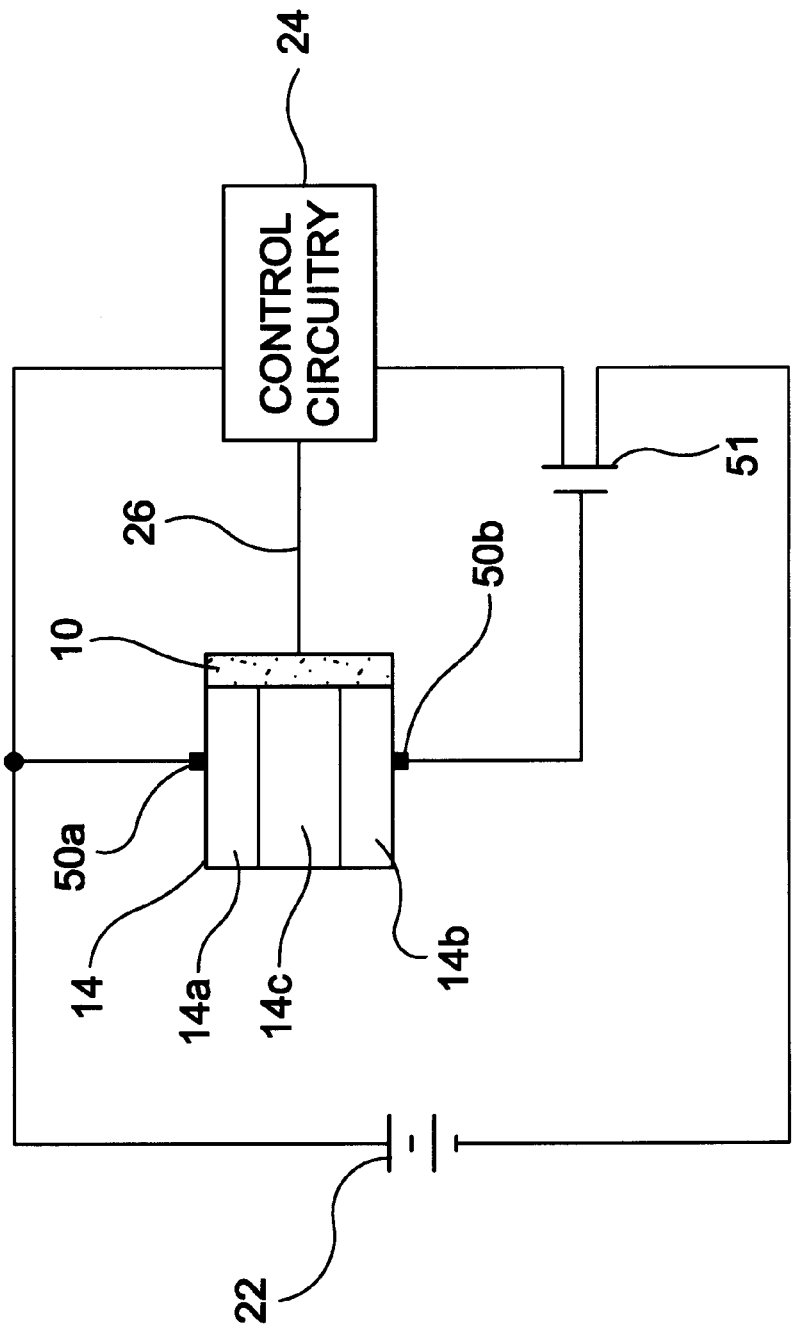
FIG. 6 shows a reservoir detection circuit in accordance with the present invention.

In yet another embodiment, connection of the power source 22 to the control circuitry 24 can be made when one or both of the drug reservoirs 14 and 20 is connected to or inserted into the controller 2. The connection of the power source 22 may also be made when the ionic drug 12 is inserted into the active reservoir 14, or by breaking one or both of the reservoirs 14 and 20 so that the ionic drug 12 is ready for delivery. For example, the ionic drug 12 or gel 16 may be sealed in a non-conductive pouch, which may be opened to release it contents. As shown in FIG. 6, the reservoir 14 (reservoir 20 may be similarly constructed) has two electrically conductive halves (14a and 14b) separated by an electrical insulator 14c. Reservoir 14 forms one hollow chamber, but halves 14a and 14b are not electrically connected. Half 14a is electrically connected to interconnection 50a which is connected to one power terminal of the power source 22. Half 14b is electrically connected to interconnection 50b which is connected to the gate of FET 51. When the reservoir 14 is filled with the ionic drug 12, halves 14a and 14b are electrically connected which biases the gate of FET 51, activating FET 51. This, in turn, connects the power source 22 to the control circuitry 24 by allowing current to flow through the source and drain of the FET 51. In this embodiment, connecting or inserting the reservoir 14 (filled with ionic drug 12) will also cause the gate of the FET 51 to be biased. However, if the reservoir 14 is inserted with the ionic drug 12 sealed in a non-conductive pouch, the gate of the FET 51 will not be biased. In this case, opening/breaking the non-conductive pouch containing the ionic drug 12 will activate FET 51 because the released ionic drug 12 will electrically short halves 14a and 14b and bias the gate of FET 51. Alternatively, the reservoir 14 may be constructed without the electrical insulator 14c. In this case, the circuit of FIG. 6 will connect the power source 22 to the controller 2 whenever the reservoir 14 (with or without the ionic drug 12) is connected or inserted into the controller 2.

In yet another embodiment, the power source 22 may be placed within the controller 2 so that the control circuitry 24 has electrical power, but is almost completely turned off. Only a small portion of the electronic circuitry shown in FIG. 3 will draw current from the power source 22, consuming, for example, only about 10 microamperes or less. The microprocessor 40 will draw current, but will be in a low-power (sleep) mode. In this embodiment, because current is being drawn at all times, the power source 22 will drain over time. But since such a small amount of current is being drawn, it will take a very long time for the power source 22 to drain, thus ensuring a long shelf life for the controller 2. This embodiment has an advantage that because power is being supplied at all times to the microprocessor 40, the microprocessor 40 can periodically wake up to perform certain housekeeping chores or maintain certain controller status information, such as the number of times the reusable controller has already been used.

In this embodiment, an activation signal circuit 28 is connected to the microprocessor 40, as shown in FIG. 3. For example, the activation signal circuit 28 may be connected to an input/output (I/O) port or an interrupt signal lead of the microprocessor 40. Normally, the microprocessor 40 will be powered up but in a sleep mode, and the control circuitry 24 will draw very little current. The microprocessor 40 is programmed to periodically wake up, for example, once a second, to read the status of the I/O port or the interrupt signal lead. A change in the read logic level (i.e., logic "ONE" to logic "ZERO") causes the microprocessor 40 to fully wake up and enter its normal operating state. The microprocessor 40, or other circuitry, turns on the remainder of the control circuitry 24.

The controller 2 is now ready to deliver current to the attached patch. (It will be appreciated that with known modification the logic values "ONE" and "ZERO" may be reversed as required, and the above embodiment is not to be limited to any particular logic scheme.) If the microprocessor 40 determines that there has been no change in the activation signal circuit 28, the microprocessor 40 returns to sleep until the next sampling interval. Alternatively, the microprocessor 40 does not have to periodically wake up to read the signal, it may automatically jump to an interrupt handling routine whenever the interrupt signal input changes logic values.

The activation signal circuit 28 may be implemented using a variety methods. Many of the types of connectors 25 discussed above may also be used as the activation signal circuit 28, such as, but not limited to, pressure switches, photoelectric devices, magnetic devices, piezoelectric materials, electromagnetic signal receivers, vibration detectors, gravity detection devices, sound detection devices, temperature detection devices, gas detection devices and drug reservoir-related activation schemes.

Figure 7A:
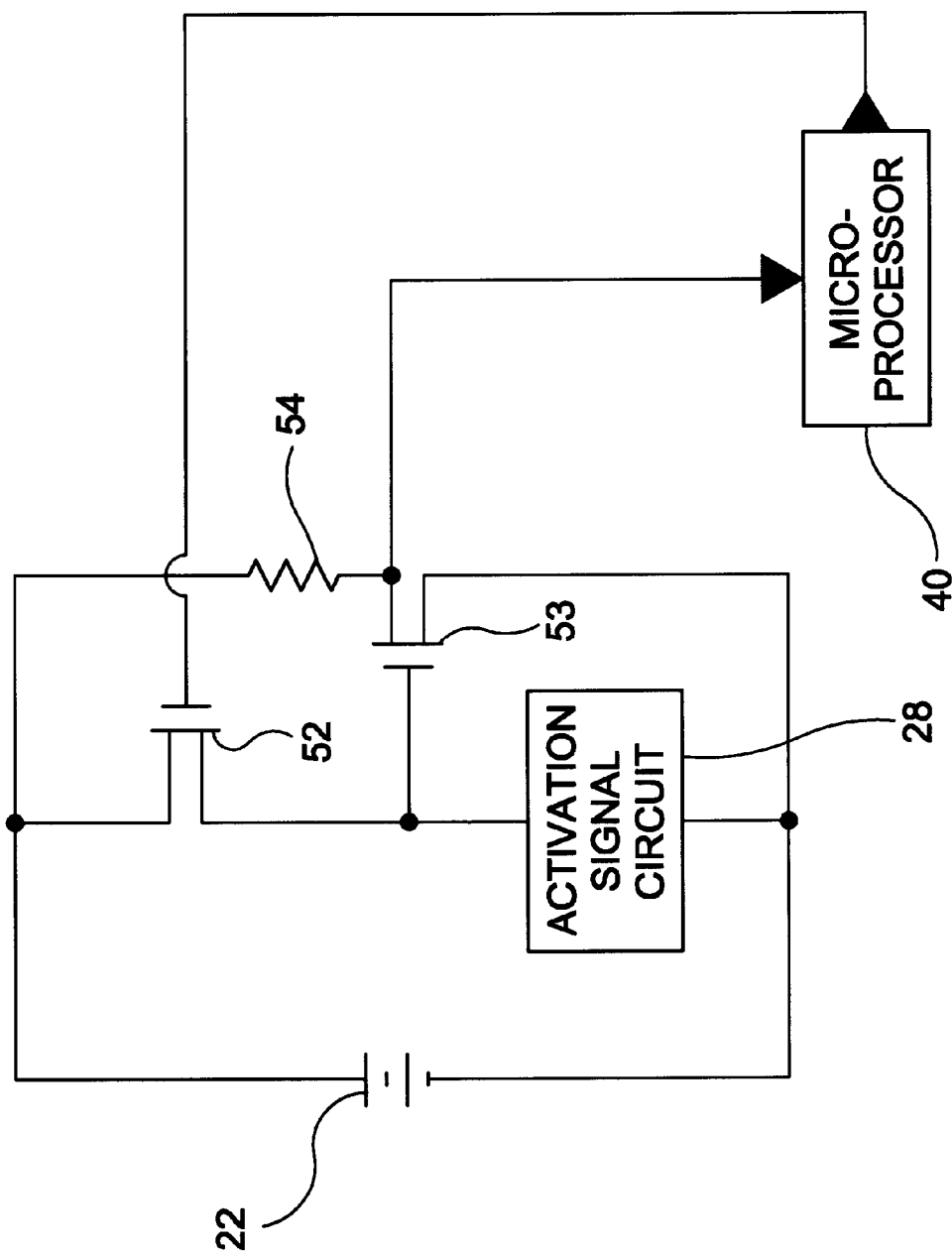
FIGS. 7A, 7B and 7C show various activation signal circuits in accordance with the present invention.

As shown in FIG. 7A, a latching circuit can be used in conjunction with the activation signal circuit 28 and the above-discussed activation methods. When the activation signal circuit 28 is triggered (for example, by light or magnetism), it biases the gate of a FET 53 (by producing an electrical current) which turns on the FET 53. The source of FET 53 is connected to the I/O port (or interrupt signal lead) of the microprocessor 40. When FET 53 is not activated (i.e., in the off state), the source is at logic "ONE" potential (i.e., tied high through pull-up resistor 54). When FET 53 is turned on, the source is essentially at a logic "ZERO" potential. The change in logic potential caused the microprocessor 40 to switch the operational state. The microprocessor 40 then biases the gate of FET 52, via an output port, which activates FET 52. FET 52 then biases the gate of FET 53 which ensures that FET 53 remains on, even if the biasing signal from the activation signal circuit 28 is removed. The microprocessor 40 can deactivate the latching circuit, after drug delivery is complete, by stopping/removing the biasing signal connected to gate of FET 52.

Figure 7C:
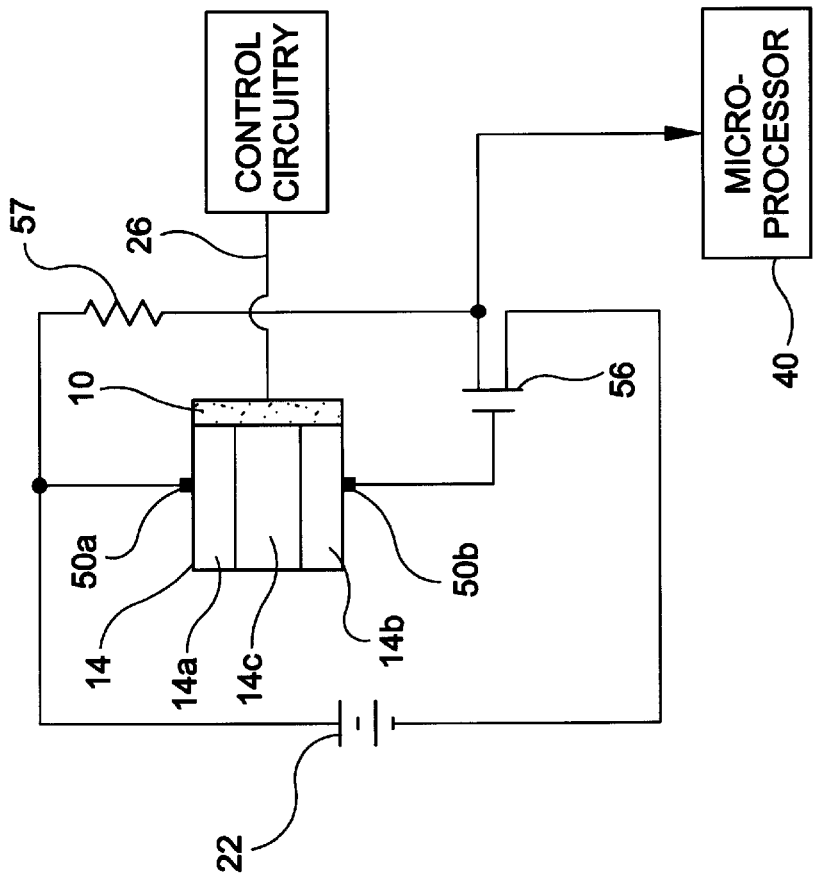
Figure 7B:
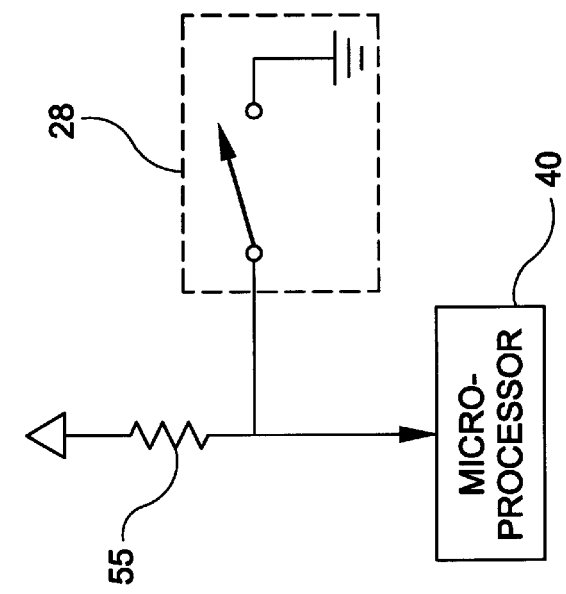

Alternatively, FIG. 7B shows a circuit diagram that may be used with the activation signal circuit 28. In particular, when the activation signal circuit 28 is not "on" (shown symbolically by an open switch), the input to the microprocessor 40 is at a logic "ONE" potential (i.e., tied high through pull-up resistor 55). When the activation signal circuit 28 is "on" (not shown, but represented by a closed switch), the input to the microprocessor 40 is at a logic "ZERO" potential.

FIG. 7C shows a circuit diagram that may be used to detect whether the reservoir 14 (and/or that the drug 12 is held in the reservoir 14) is connected to the iontophoretic drug delivery device. When the gate of FET 56 is biased by the current flowing through reservoir 14, FET 56 activates. This changes the logic potential at the source of FET 56 from ONE to ZERO. When the FET 56 is not active, the source is at logic ONE (i.e., tied high through pull-up resistor 57).

In addition, other activation signal circuit 28 may be used. As discussed below, many types of medical test results/signals/waveforms and bodily function indicators may be used to trigger the activation signal circuit 28.

The activation signal circuit 28 may be triggered based on information from photometric waveforms, such as from a photoplethysmography system or a pulse oximeter, electrocardiograph (EKG) signatures (i.e., heart-related waveforms), blood-gas test signals (partial pressure of $CO_2$ or $O_2$), electromyograph (EMG) signals (i.e., muscle-related waveforms) and blood glucose monitor readings. It is well known, for example, that glucose levels in the subcutaneous tissue closely correlate with blood glucose levels in the body. Therefore, delivery of insulin as required by the patient's body may be based on the use of subcutaneous glucose levels of the patient to trigger the activation signal circuit 28. The above signatures, signals, readings, and the like are generated by external devices 29 (as shown in FIG. 3), which also analyze them. When a predetermined reading, condition or error is detected, the external device 29 sends an activation signal to the activation signal circuit 28 to turn on the iontophoretic drug delivery device. The activation signal from the external device 29 may be sent by switching a relay, closing a switch, or any of the other connectors 25 discussed above. Alternatively, the information may be generated and analyzed by devices or circuitry (e.g., a miniature heart rate or blood glucose monitor) internal to the iontophoretic drug delivery device.

The external device 29 may also include a barcode reader. The signal from the barcode reader can be used, for example, to activate automatically the iontophoretic drug delivery device or set a timer delay to activate the device. The barcode reader can also be used for other purposes such as providing information concerning a specific prescription drug, which is used by the device to accurately deliver the drug.

The activation signal circuit 28 may also be triggered based on changes in the user's skin hydration using a skin-moisture sensor. In this case, the iontophoretic drug delivery device activates only when the impedance of the user's skin 6 has reduced sufficiently from hydration (i.e., after the patch 4 has been attached to the skin 6 for a period of time, the skin will being to hydrate). As discussed above, an extremely dry skin-patch interface may result in higher electrical impedance, which in turn may reduce drug transport and cause skin irritation.

As discussed in the Background Section, the pH level of a user's skin or perspiration may also affect the iontophoretic delivery of peptides. Accordingly, the activation signal circuit 28 may also be triggered based on the skin's pH or the amount of perspiration thereon by respectively using the output of a pH or perspiration indicator.

It will be appreciated that many of the connector 25 and activation signal circuit 28 discussed above may be combined. For example, an external EKG monitor may be connected to an iontophoretic drug delivery device via a fiber optic cable. When the EKG monitor detects a predetermined trigger condition, it sends an activation signal via the fiber optic cable to the device's activation signal circuit 28. A connector 25 comprising a photodetector is used by the iontophoretic device to detect the activation signal and to cause the start of drug delivery. Of course, many other combinations of the various connectors 25 and activation signal circuits 28 are possible, as will be appreciated by those skilled in the art.

Alternatively, the controller 2 may be kept fully powered at all times once the power source 22 is inserted into the controller. In this embodiment, the need for an on/off switch using a connector 25 and/or activation signal circuit 28 is eliminated, thus reducing the overall cost of the iontophoretic drug delivery device. Because current is being drawn at all times, the power source 22 will drain over time. However, the battery drain can be reduced by inserting the power source 22 in the controller 2 just prior to being given or sold to a user. For example, a health-care provider can assemble the device before giving it to a patient. The power source 22, of course, can be inserted at the time of manufacture of the device. This embodiment has an advantage compared to the other embodiments in that since power is being supplied at all times to the microprocessor, the microprocessor can periodically perform certain housekeeping chores or maintain certain controller status information, as discussed above with respect to the other embodiments (i.e., such as the number of times the controller has been used and to check drug validation information such as expiration dates). In addition, the device is less expensive to manufacture because fewer components are used.

Of course, it will be appreciated that the invention may take forms other than those specifically described, and the scope of the invention is to be determined solely by the following claims.

What is claimed is:

1. An iontophoretic drug delivery device comprising:

a controller having a current generating circuit, said controller having an operational state, a normally off state and being selectively switchable between the states;

a power source;

a patch attachable to the skin of a subject, the patch comprising at least two reservoirs respectively including an anode and a cathode, one of the reservoirs for holding an ionizable drug for transcutaneous delivery when said controller is in the operational state and said patch is attached the skin, said patch being removably, electrically connectable to said controller;

a connector having one end and another end for electrically connecting said power source to said controller, and wherein when said patch is electrically connected to said controller and said connector connects said power source to said controller, said controller is switched to the operational state from the normally off state; and wherein said connector comprises a pull tab comprising a material that is an electrical insulator, said pull tab being inserted between said power source and said controller such that when said pull tab is removed said power source is electrically connected to said controller.

2. A device according to claim 1, wherein said connector further comprises a switch having make/break contacts, said pull tab being inserted said between make/break contacts of the switch thereby to prevent the switch from operating, the switch being connected between said power source and said controller, wherein when said pull tab is removed thereby removing said electrical insulator, the switch is operational for selectively electrically connecting said power source to said controller.

3. An iontophoretic drug delivery device comprising:

a controller having a current generating circuit, said controller having an operational state, a normally off state and being selectively switchable between said operational and said normally off state, said controller having a signal terminal, a first battery terminal and a second battery terminal;

a patch attachable to the skin of a subject, the patch comprising at least two reservoirs respectively including an anode and a cathode, one of the reservoirs for holding an ionizable drug for transcutaneous delivery when said controller is in an operational state and said patch is attached the skin, said patch being removably, electrically connectable to said controller;

a power source having power terminals;

a connector for electrically connecting said power terminals to said controller, said controller thereby being switched to the operational state when said patch is electrically connected to said controller;

wherein said connector includes a latch circuit for latching said power terminals to said controller when triggered by a trigger source;

wherein said power source includes a first power terminal and a second power terminal, and the latch circuit includes a first FET and a second FET each having a gate, a drain and a source, the gate of the first FET being connected to the trigger source and the drain of the second FET, the drain of the first FET being connected to the first power terminal, the source of the first FET being connected to said first battery terminal of said controller, and said second battery terminal of said controller being connected to the second power terminal, the gate of the second FET being connected to said signal terminal of said controller, and the source of the second FET being connected to the second power terminal, wherein when the gate of the first FET is biased by a signal from the trigger source, the first FET activates allowing current to flow through its source and drain, essentially connecting the first battery terminal of said controller to the first power terminal such that power is supplied to said controller, the gate of the second FET is then biased by a signal from said controller, turning on the second FET, and wherein the gate of the first FET is then biased by the second FET even if the signal from the trigger source is removed.

4. An iontophoretic drug delivery device comprising:

a controller having a current generating circuit, said controller having an operational state, a normally off state and being selectively switchable between said operational and said normally off state, said controller having a signal terminal, a first battery terminal and a second battery terminal;

a patch attachable to the skin of a subject, the patch comprising at least two reservoirs respectively including an anode and a cathode, one of the reservoirs for holding an ionizable drug for transcutaneous delivery when said controller is in an operational state and said patch is attached the skin, said patch being removably, electrically connectable to said controller;

a power source having power terminals;

a connector for electrically connecting said power terminals to said controller, said controller thereby being switched to the operational state when said patch is electrically connected to said controller;

wherein said connector includes a latch circuit for latching said power terminals to said controller when triggered by a trigger source;

wherein said connector further comprises drug detection means for detecting that the ionizable drug is held within at least one of the reservoirs and wherein at least one of the reservoirs consists of a chamber formed by a first electrically conductive half and a second electrically conductive half, the first and second halves being physically connected by an electrical insulator, where said connector connects the power source to said controller when said drug detection means detects that the ionizable drug is held within one of the reservoirs;

wherein said drug detection means comprises a FET having a gate, a drain and a source, the gate being connected to the first half, the drain being connected to a first battery terminal of said controller, the source being connected to the first power terminal, the second power terminal being connected to the second half and a second battery terminal of said controller; and where when the ionizable drug is held within the chamber of the reservoir, the gate of the FET is biased by a current passing through the chamber, activating the FET and allowing current to flow through the drain and source, essentially connecting the first battery terminal of said controller to the first power terminal such that power is supplied to said controller.

5. A device according to claim 4, wherein at least one the reservoirs is removable from said device.

6. A device according to claim 4, wherein said connector further comprises reservoir detection means for detecting that at least one of the reservoirs is connected to said device, where said connector connects the power terminals to said controller when the reservoir detection means detects that at least one of the reservoirs is connected to said device.

7. An iontophoretic drug delivery device comprising:

a controller having a current generating circuit, the controller normally being in a low power consumption state when connected to a power source and an operational state, said controller being selectively switchable between said low power consumption state and said operational state;

a patch attachable to the skin of a subject, the patch comprising at least two reservoirs respectively including an anode and a cathode, one of the reservoirs for holding an ionizable drug for transcutaneous delivery when the controller is in an operational state and when the patch is attached to the subject's skin, the patch being removable and electrically connectable to the controller;

activation signal means for signaling the controller to switch the operational state;

wherein the activation signal means includes latching means for latching a momentary activation signal;

wherein the latching means includes a first FET and a second FET, each having a gate, a drain and a source, the gate of the first FET being connected to the activation signal means and the drain of the second FET, the drain of the first FET being connected to a first terminal of the power source, the source of the first FET being connected to a signal input port of the controller, the gate of the second FET being connected to an output signal port of the controller, wherein when the gate of the first FET is biased by an activation signal from the activation signal means, the first FET activates, changing a logic potential of the source of the first FET, the controller being switched to the operational state in response to the logic potential change, and wherein the gate of the second FET being then biased by a signal from the controller so that the second FET activates, the gate of the first FET being then biased by the second FET even if the activation signal is removed.

8. An iontophoretic drug delivery device comprising:

a controller having a current generating circuit, the controller normally being in a low power consumption state when connected to a power source and an operational state, said controller being selectively switchable between said low power consumption state and said operational state;

a patch attachable to the skin of a subject, the patch comprising at least two reservoirs respectively including an anode and a cathode, one of the reservoirs for holding an ionizable drug for transcutaneous delivery when the controller is in an operational state and when the patch is attached to the subject's skin, the patch being removable and electrically connectable to the controller;

activation signal means for signaling the controller to switch the operational state;

wherein the activation signal means includes latching means for latching a momentary activation signal;

wherein at least one of the reservoirs consists of a chamber formed by a first electrically conductive half and a second electrically conductive half, the first and second halves being physically connected by an electrical insulator, where the reservoir detection means comprises a FET having a gate, a drain and a source, the gate being connected to the first half, the source of the FET being connected to a first terminal of the power source, a signal input port of the controller and the second half, the drain being connected to a second terminal of the power supply, and where when the ionizable drug is held within the chamber of the reservoir, the gate of the FET is biased by a current passing through the chamber, which will activate the FET, changing the logic potential of the source of the FET, wherein the controller switches to the operational state in response to the change in logic potential.

* * * * *